US008857058B2

(12) United States Patent
Gagnon et al.

(10) Patent No.: US 8,857,058 B2
(45) Date of Patent: Oct. 14, 2014

(54) METHOD AND SYSTEM FOR MAKING DENTAL RESTORATIONS

(75) Inventors: Jean Gagnon, Quebec (CA); Louis Gagne, Quebec (CA); Oleg Boulanov, Quebec (CA)

(73) Assignee: Dental Wings Inc., Montreal (CA)

( * ) Notice: Subject to any disclaimer, the term of this patent is extended or adjusted under 35 U.S.C. 154(b) by 179 days.

(21) Appl. No.: 13/582,892

(22) PCT Filed: Mar. 9, 2011

(86) PCT No.: PCT/CA2011/000270
§ 371 (c)(1),
(2), (4) Date: Sep. 7, 2012

(87) PCT Pub. No.: WO2011/109906
PCT Pub. Date: Sep. 15, 2011

(65) Prior Publication Data
US 2012/0324731 A1  Dec. 27, 2012

Related U.S. Application Data

(60) Provisional application No. 61/282,630, filed on Mar. 9, 2010.

(51) Int. Cl.
| B23P 13/00 | (2006.01) |
| B23K 26/08 | (2014.01) |
| B23K 26/14 | (2014.01) |
| A61C 13/00 | (2006.01) |
| B23K 26/12 | (2014.01) |
| B23K 26/03 | (2006.01) |
| G05B 19/4099 | (2006.01) |
| B23K 26/04 | (2014.01) |

(52) U.S. Cl.
CPC ........ *G05B 19/4099* (2013.01); *B23K 26/0861* (2013.01); *G05B 2219/49328* (2013.01); *G05B 2219/37048* (2013.01); *G05B 2219/45167* (2013.01); *G05B 2219/37042* (2013.01); *B23K 26/14* (2013.01); *A61C 13/0004* (2013.01); *B23K 26/127* (2013.01); *G05B 2219/49087* (2013.01); *A61C 13/0018* (2013.01); *B23K 26/0846* (2013.01); *B23K 26/032* (2013.01); *B23K 26/04* (2013.01)

USPC ........................................................ 29/896.1

(58) Field of Classification Search
CPC ............ B23P 6/00; B23P 6/04; G01B 11/25; G06T 7/0057; A61C 13/0004; A61C 13/0018; B23K 26/32; B23K 26/04; B23K 26/0846; B23K 26/0861; B23K 26/14; B23K 26/127; G05B 19/4099; G05B 2219/49328; G05B 2219/37042; G05B 2219/37048; G05B 2219/45167
USPC .............. 29/896.1, 721, 712, 402.01, 402.05, 29/402.06; 356/603, 608; 382/154; 433/215; 600/476, 590; 219/121.83, 219/121.78, 121.84
See application file for complete search history.

(56) References Cited

U.S. PATENT DOCUMENTS 5,685,999 A    11/1997  Wiedemann et al.
7,835,558 B2 * 11/2010  Gagnon et al. ................ 382/128

FOREIGN PATENT DOCUMENTS

WO   2009/073376 A1   6/2009

*Primary Examiner* — John C Hong
(74) *Attorney, Agent, or Firm* — BCF LLP

(57) ABSTRACT

A system for making a dental restoration, comprising a 3D digitizer for producing a 3D model digital representation of a dental restoration model, a computer in communication with the 3D digitizer and capable of creating a dental restoration milling trajectory for a selected block of given dimension and given dental restoration material, based on the 3D model, and a laser milling apparatus in communication with the computer and capable of laser milling the dental restoration from the selected block positioned therein using the milling trajectory created by the computer. The laser milling apparatus includes one or more sensor for continuously monitoring the laser milling of the selected block and to provide feedback to the computer such that the milling trajectory is continuously adjusted by the computer using the feedback from the one or more sensor.

14 Claims, 3 Drawing Sheets

METHOD AND SYSTEM FOR MAKING DENTAL RESTORATIONS

CROSS-REFERENCE TO RELATED APPLICATION

The present application claims the benefits of U.S. provisional patent application No. 61/282,630 filed Mar. 9, 2010, which is hereby incorporated by reference.

TECHNICAL FIELD

The present disclosure relates to method and system for making dental restorations.

BACKGROUND

Dental restorations are used as permanent implants to fill the damage from dental cavities or from other causes. Commonly used dental restorations include inlays, onlays, dentinal pins and root pins. For example, an inlay is used to fill a tapered recess defined across an upper portion of a tooth. Dental restorations can be made of various durable materials including metals, composites, ceramics and porcelains and can be molded or machined. The quality of the dental restoration is typically related to its shape, its aesthetics and its durability.

Known methods and systems for making dental restorations such as inlays and onlays typically involve creating the dental restoration from a model or mold in a remote lab. The patient takes an appointment for a first visit with his dentist during which the dentist takes an impression of the missing dental tissue. In the case of some restorations, the dentist then fills the damaged region with a temporary fill material. In some cases, these manipulations require anesthesia. The patient then returns home with the temporary fill and the impression is sent to a remote lab where the dental restoration is made by a lab technician, using the impression. The dental restoration is then sent to the dentist.

The patient then takes another appointment for a second visit with his dentist. Some temporary fills have been known to fail between the two visits. In the second visit, the dentist can remove the temporary fill and prepare the damaged region of the tooth to receive the dental restoration. In some cases, this requires a second anesthesia. It is often required that the dentist make final adjustments to the dental restoration to adapt the contours of the restoration to the opposite teeth when the jaw is closed. In some cases, due to occurrence of errors stemming from the several manipulations by the dentist and/or by the remote lab technician, the restoration does not fit, and the process has to be repeated.

One of the latest techniques is the use of inlay-onlays prepared using 3D software such as, for example, the CEREC system from Sirona. The method consists in coating the tooth with a white powder and using a 3D imaging camera to upload a 3D representation of the tooth into a computer for executing a virtual restoration. The data obtained from the virtual restoration is stored in a file and is sent to a milling machine. The inlay-onlay is then milled out of a solid ceramic or composite block. Most inlay-onlays are made tooth-colored porcelain. However, these systems have some important drawbacks, mainly:

- the milling tool drill bits and block may break because of increased strain against the block, forcing the user to change them often;
- necessitate dentists to digitally create the model from scans, which is time consuming and requires computer-aided design (CAD) skills for which dentists are not normally trained;
- having to use a CAD platform in order to generate a tool path is very complex; and
- the complex environmental constraint in which the 3D data is obtained with the help of an intra-oral scanner doesn't allow for accurate measurement of the occlusal, therefore creating inaccuracies in the finished restoration.

The known methods and systems described above have been used for years and have provided a certain degree of satisfaction to its users. However, these methods and systems have been known to suffer from several drawbacks, including the discomfort to the patient caused by the presence of two distinct appointments. There thus remained room for improvements.

SUMMARY

The present disclosure relates to a system for making a dental restoration, comprising
  a 3D digitizer for producing a 3D model digital representation of a dental restoration model;
  a computer in communication with the 3D digitizer and capable of creating a dental restoration milling trajectory for a selected block of given dimension and given dental restoration material, based on the 3D model; and
  a laser milling apparatus in communication with the computer and capable of laser milling the dental restoration from the selected block positioned therein using the milling trajectory created by the computer, the laser milling apparatus including one or more sensor for continuously monitoring the laser milling of the selected block and provide feedback to the computer;
wherein the milling trajectory is continuously adjusted by the computer using the feedback from the one or more sensor.

The present disclosure also relates to a laser milling apparatus for laser milling a block of material in accordance with a milling trajectory, comprising:
  one or more laser;
  optics associated with the one or more laser;
  a milling chamber having therein a multi-axis displacement mechanism for supporting and displacing the selected block;
  one or more controller for controlling the optics and the multi-axis displacement mechanism in accordance with the milling trajectory;
  one or more sensor to continuously monitor the laser milling of the block and provide feedback to the laser milling apparatus;
wherein the milling trajectory is continuously adjusted by the laser milling apparatus using the feedback from the one or more sensor.

The present disclosure also further relates to a method for making a dental restoration, comprising
  producing a 3D model digital representation of a dental restoration model;
  selecting a block of dental restoration material having a size sufficient to encompass the dental restoration;
  creating a dental restoration milling trajectory of the dental restoration for the selected block based on the 3D model;
  positioning the selected block in the a laser milling apparatus;
  laser milling the dental restoration from the selected block in accordance with the milling trajectory; and continuously monitoring the laser milling of the selected block and adjusting the milling trajectory based on feedback provided by the monitoring of the laser milling of the selected block.

BRIEF DESCRIPTION OF THE FIGURES

Embodiments of the disclosure will be described by way of example only with reference to the accompanying drawings, in which.

DETAILED DESCRIPTION

Figure 1:
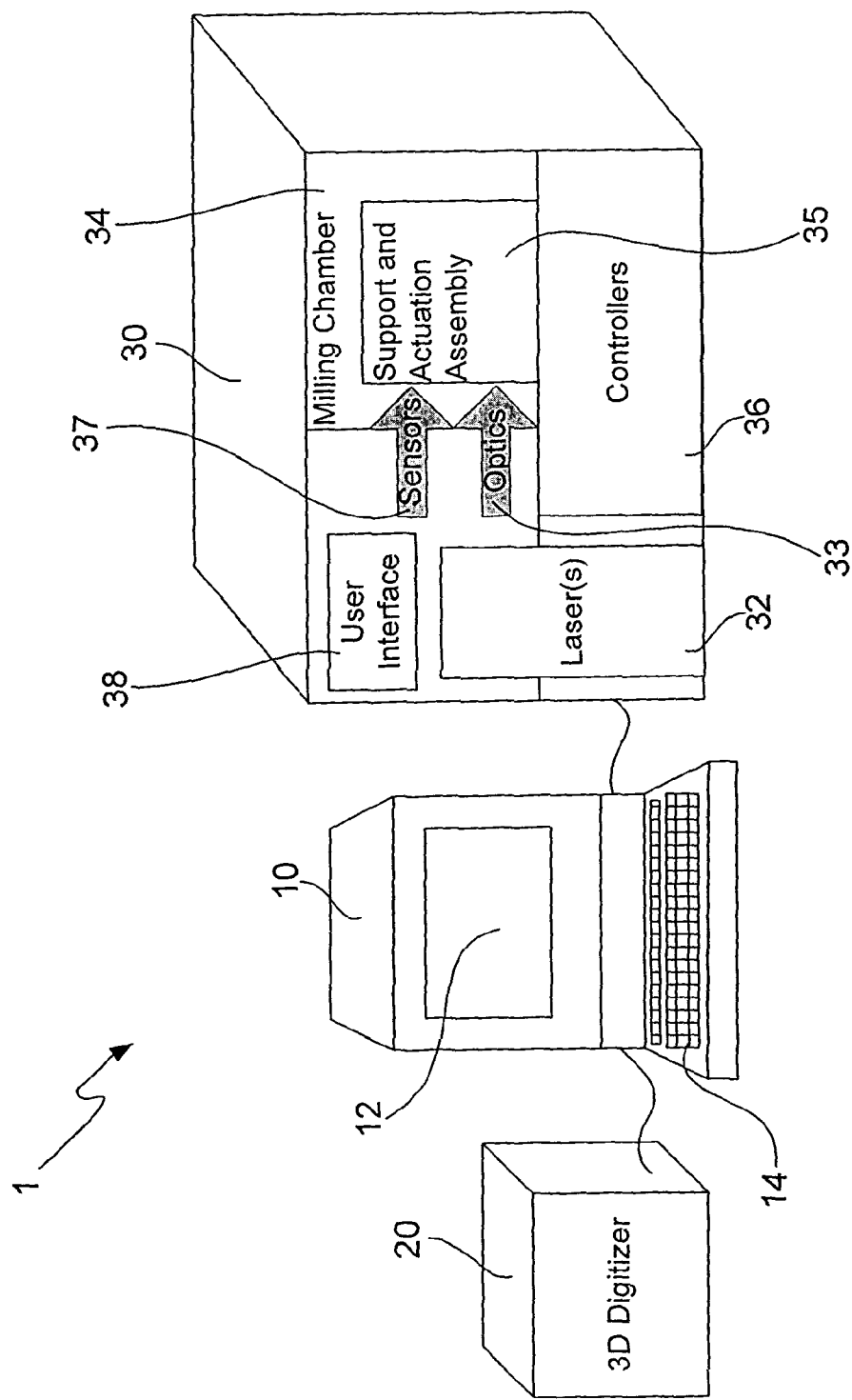
FIG. 1 is a schematic view of an improved system for making a dental restoration in accordance with an illustrative embodiment of the present disclosure.

Generally stated, the non-limitative illustrative embodiment of the present disclosure provides a method and system for making dental restorations. A model of the dental restoration is shaped in-vivo, in the patient's mouth by the user (e.g. dentist, dental technician, etc.) using an easy to manipulate material. The in-vivo model is then extracted from the mouth of the patient and digitized in the user's office using a 3D digitizer. An accurate three-dimensional (3D) digital representation of the model is then obtained. The system then extrapolates the various parameters necessary to generate an initial milling trajectory which will be used to replicate a block of dental restoration material into the shape of the in-vivo model. Optimally, the system tries to determine the milling trajectory that maximizes the material removed while minimizing the distance traveled. This milling trajectory is continuously adjusted during the milling process using feedback from sensors monitoring the dimensional evolution of the milled block. The laser milling apparatus located either in the user's office or remotely located, replicates the dental restoration while the patient is waiting. The user can then take the laser milled dental restoration and apply it to the patient in the same, single visit. Types of dental restorations which can be made by the present method and system include dentinal pins, root pins, inlays, onlays and crowns.

Since the dental restoration system uses non-contact milling, its mechanical structure is simplified because of the limited impact of machine vibration, it doesn't need coolant or bit replacement and provides greater possibility of customization such as, for example, the use of specific laser wavelengths for specific types of materials instead of having to change physical drill bits.

The use of an in-vivo model of the restoration shaped directly in the patient's mouth helps maintain to a minimum the number of manipulations from the shaping of the model to the milling of the dental restoration, and helps reduce the risks of error. Furthermore, by shaping the model directly in the patient's mouth, the user can verify prior to the creation of the dental restoration that it will not interfere with the other teeth when the jaw of the patient is closed.

The dental tissue to which the dental restoration is to be applied is prepared by defining a tapered recess therewithin. A hardening compound is then applied to the tapered recess in-vivo by the dentist, and the compound is hardened.

The model can be made of many types of hardening compounds. One example of such a material is a material which hardens under ultraviolet radiation. In the illustrative embodiment, the hardening material is non-adhesive, in order to be easily removable, and can be removed due to the tapered shape of the recess in the dental tissue. If desired, a layer of adhesion-preventing compound can be applied to the dental tissue prior to application of the hardening compound to prevent adhesion between the hardening compound and the dental tissue.

If shrinkage occurs during hardening, or if an adhesion-preventing compound is used, the resulting in-vivo model will typically be slightly smaller than the volume of the missing dental tissue. This can be beneficial Dental restorations typically require application of an adhesive to adhere the dental restoration to the dental tissue. The layer of adhesive has a thickness, and if the dental restoration is of the exact shape and size than the missing dental tissue, the thickness of the adhesive may cause the dental restoration to not properly fit the tapered recess. If just the right amount of shrinkage occurs during hardening, the in-vivo model may be sized just perfectly to allow for the thickness of the layer of adhesive. The dental restoration can then be made with the exact size and shape than the in-vivo model and it will be ready to be applied to the patient using a layer of adhesive.

A way of obtaining an in-vivo model which has the right size to allow for the layer of adhesive when the hardening compound does not shrink during hardening is to apply a layer of a spacing compound having the thickness of a layer of adhesive to the surface of the tapered recess before applying the hardening compound. The resulting in-vivo model will have the volume of the missing dental tissue minus the thickness of the spacing compound. The spacing compound can advantageously be a non-adhesive compound to help prevent unwanted adhesion between the model and the dental tissue in cases where this can occur.

If the in-vivo model does not allow sufficient spacing with the dental tissue for a layer of adhesive, it is also possible to electronically modify the 3D model of the digitized in-vivo model to offset or scale the surfaces which will be in contact with the dental tissue. The surfaces of the dental restoration or in-vivo model, which are adjacent the dental tissue, are referred to herein by the term adhesion surfaces. The dental restoration can then be based on the electronically modified image and be adapted for the layer of adhesive.

Referring to FIG. 1, there is shown an example of a dental restoration system 1 which can be used in a dentist's office to digitize the in-vivo model and replicate its dimensions and shape from a block of dental restoration material using laser milling. The dental restoration system 1 includes a computer (or computing device, processor with associated memory, etc.) in communication with a 3D digitizer 20 and a laser milling apparatus 30. The laser milling apparatus 30 includes one or more laser(s) 32, with associated optics 33, a milling chamber 35 having therein a support and actuation assembly 35, one or more controller(s) 36, sensors 37 and a user interface 38. The components of the dental restoration system 1 can be provided in separate rooms or in a single room. For instance, the computer 10 and 3D digitizer 20 can be provided in an operation room, while the laser milling apparatus 30 is placed in another room. Alternatively, computer 10, 3D digitizer 20 and laser milling apparatus 30 can be provided together as a single, stand-alone unit. The computer 10 includes a display 12 to allow the visualization and manipulation of the 3D model obtained by the 3D digitizer 20, and a user interface, for example a keyboard 14 and mouse, or, alternatively, the display 12 itself in the form of a touch screen.

In an exemplary mode of operation, the display 12 can prompt the user to place the in-vivo model in the 3D digitizer 20. When the computer 10 detects that the in-vivo model is positioned in the 3D digitizer 20, the display 12 can request an input from the user to start the replicating process. The user can respond using the user interface 14, and the computer 10 commands the 3D digitizer 20 to start digitizing the in-vivo model.

The 3D digitizer 20 may be, for example, a structured light digitizer, a laser line scanner, a 3D photogrammetric scanner or a camera allowing accurate 3D measurements of the in-vivo model. It is to be understood that other types of 3D digitizers may also be used.

Once the in-vivo model is digitized, an accurate 3D model digital representation of the in-vivo model is obtained, including occlusion, without the user having to digitally/manually design the final model like is the case when using a CEREC or E4D system. The dental restoration system 1 can then propose, through the computer 10 display 12, a block of durable dental restoration material having a sufficient size to encompass the dental restoration to be laser milled by the laser milling apparatus 30. Various types, shapes, colors and sizes of blocks can be used and suggested by the dental restoration system 1. The user can then select the proposed size of block and place it in the laser milling apparatus 30 or, in an alternative embodiment, the laser milling apparatus 30 can automatically place the block in the support and actuation assembly 35. In a further alternative embodiment, the various types, shapes, colors and sizes of blocks can be stored in the laser milling apparatus 30 and selected by the user using the computer 10 user interface or laser milling apparatus 30 user interface 38.

The dental restoration system 1 determines which laser parameters, displacement speed and milling trajectory will be used to obtain an accurate copy of the in-vivo model from the selected block. The milling trajectory is communicated to the laser milling apparatus 30, which can then laser mill the dental restoration from the block. Once the laser milling of the dental restoration is completed, the dental restoration can be applied to the waiting patient. The patient can thus go home with its dental restoration and does not need to come again for another visit.

Prior to starting the laser milling, if modifications are to be made to the 3D model in order to obtain a better restoration fit, or to provide spacing for the layer of adhesive, these can be made using the computer 10 display 12 and user interface 14. This process can be partially automated, or entirely user executed. The 3D model then becomes a 3D representation of the dental restoration to be laser milled. The dental restoration system 1 then verifies if it is possible to fit the 3D representation in the selected block. If the verification is negative, the display 12 can indicate to the user to place a larger block in the machine, or alternatively the dental restoration system 1 may automatically indicate to the laser milling apparatus 30 to place a larger block in the support and actuation assembly 35. If this verification is positive, the dental restoration system 1 can send a command to the laser milling apparatus 30 to start.

Figure 2:
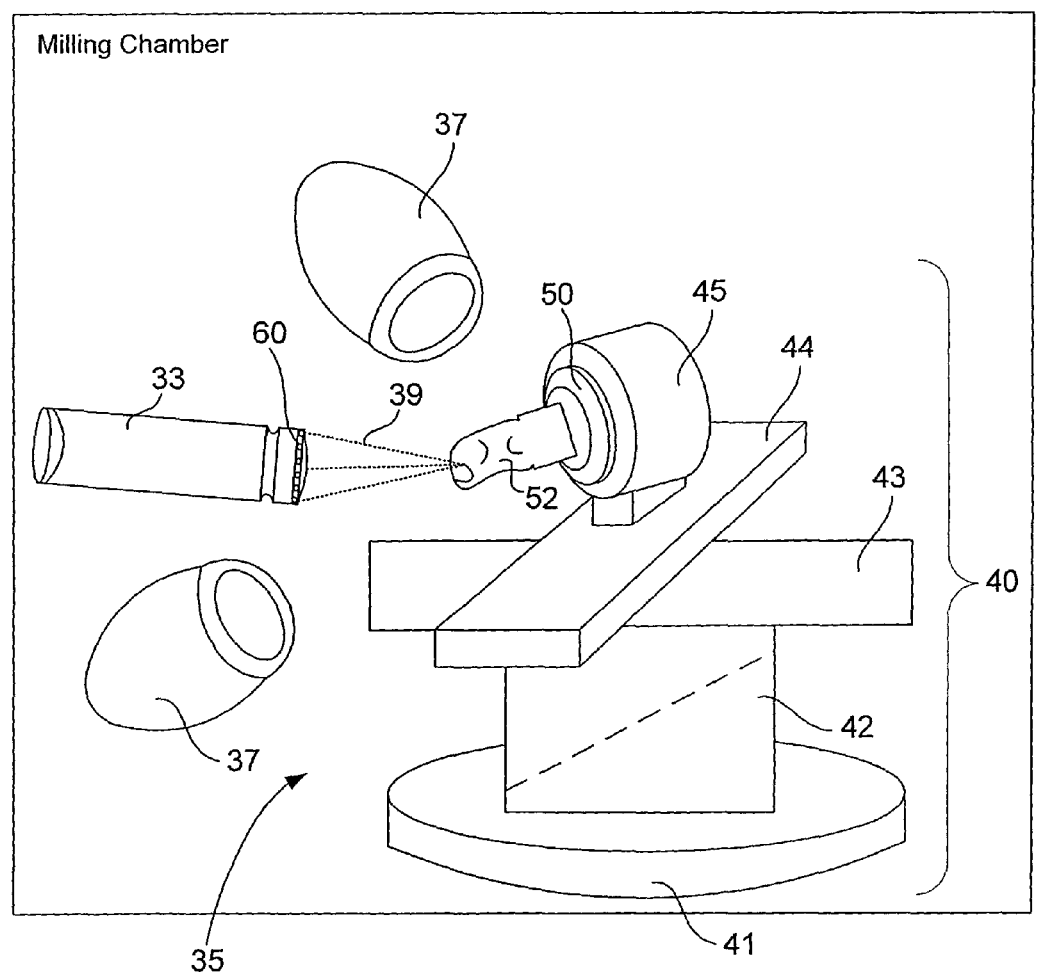
FIG. 2 is a schematic view showing detailed view of the milling chamber and its components.

The laser milling apparatus 30 is a 3D computerized numerical control (CNC) machine which can be operated in accordance with automatically computed milling trajectories. As mentioned previously, the laser milling apparatus 30 includes one or more laser(s) 32, with associated optics 33, a milling chamber 34 having therein a support and actuation assembly 35, controller(s) 36, sensors 37 and a user interface 38. Referring now to FIG. 2, the milling chamber 34 encloses the laser optics 33, the sensors 37 and the support and actuation assembly 35. The support and actuation assembly 35 is composed of a block holder 50, for holding the dental restoration material block 52, mounted on a multi-axis displacement mechanism 40. The multi-axis displacement mechanism 40 provides a sufficient degree-of-freedom so as to allow the complete milling of a freeform part, i.e. dental restoration. Actuator movements of the multi-axis displacement mechanism 40 are electronically controlled by the controller(s) 36 from parameters provided by the milling trajectory. Feedback information is provided by the sensors 37 which may be, for example, optic detectors, laser scanners, stepper motors, encoders, position rulers or a combination of thereof.

In an alternative embodiment, some or all of the functionalities of the computer 10 may be incorporated into the laser milling apparatus 30, in which case the laser milling apparatus 30 is provided with the necessary processor and associated memory.

The block 52 is precisely laser milled using a laser beam 39. The laser beam 39 is focused using appropriate convergent lenses and optics 33 under control of the controller(s) 36. The optics 33 are protected using a pressure differential air nozzle 60. The focal point of the laser beam 39 is static and it is the block 52 that moves. In the illustrative embodiment, the multi-axis displacement mechanism 40 includes three linear and two rotational axis actuators; namely a first rotational axis actuator 41, a vertical axis actuator 42, a first 43 and second 44 horizontal axis actuators and a second rotational as actuator 45. The optics 33 may comprise various lenses, mirrors or other optic components used to direct, modify, focus or change the laser beam 39 characteristics. For example, a Pi-Shaper lens or a beam expender may be used prior to focus. In an alternative embodiment, the multi-axis displacement mechanism 40 may be applied to some or all of the optics 33 components and/or to the block holder 50. It may comprise multi-axis parallel actuators such as hexapods, linear actuators and rotational actuators.

The laser beam 39 can be focused or not and may be generated from one or more laser(s) 32. The laser(s) 32 may be, for example, a $CO_2$ gas laser, a fibre laser or a combination. It is to be understood, however, that other lasers may be used and that the choice of the laser depends on the particular application and the material used for block 52. For example, $CO_2$ lasers may be used for biomaterial milling, excimer lasers for various 3D semiconductor parts for advanced electronics, fluor lasers for stone milling, art, etc., and iodine oxide lasers for different materials, composites and alloys.

In the illustrative embodiment, the block 52 is preferably made of a durable dental restoration material such as, for example, Z100 restorative dental composite from 3M™. Other materials may be used, for example ceramic, gold, titanium, etc., which will have an effect on the laser(s) 32 used.

Figure 3:
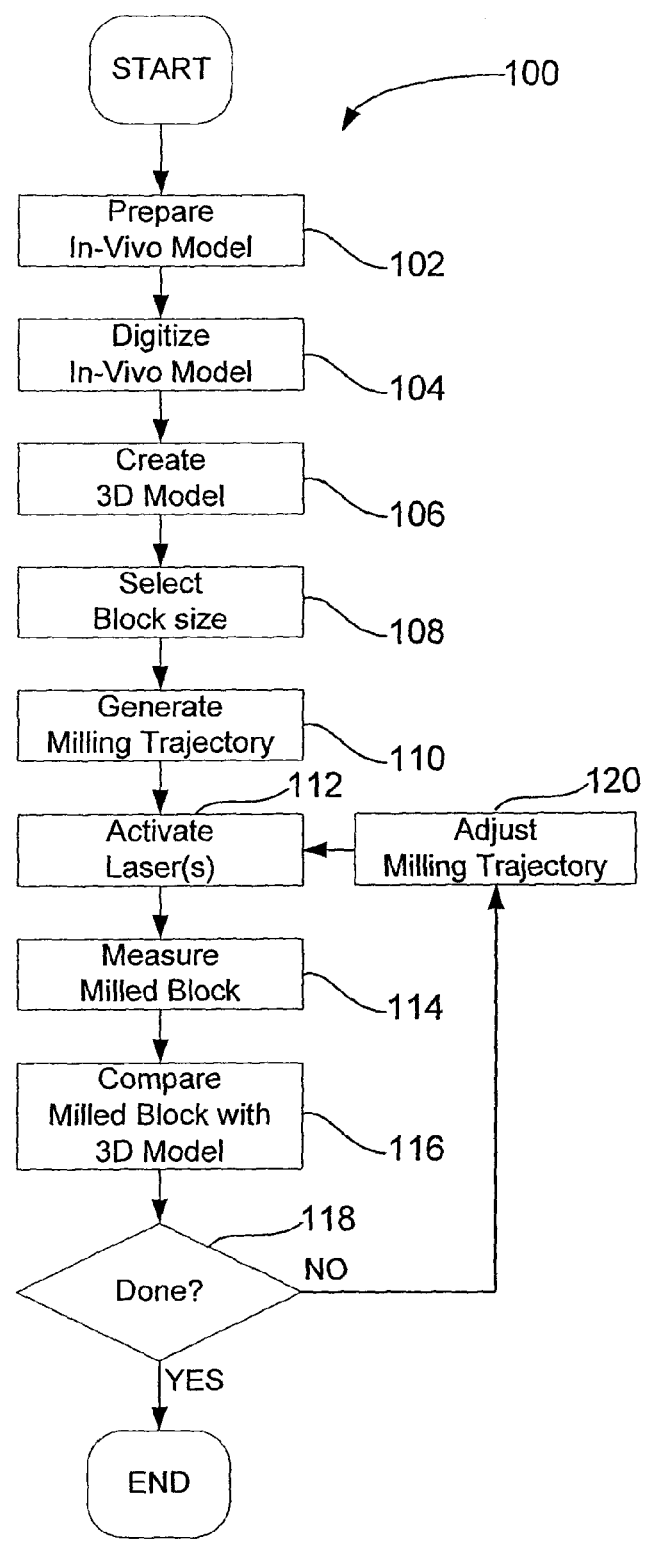
FIG. 3 is a flow diagram depicting the dental restoration procedure.

Referring now to FIG. 3, there is shown a flow diagram of an illustrative example of the dental restoration procedure 100, with references to FIGS. 1 and 2. The steps of the procedure 100 are indicated by blocks 102 to 120.

The process starts at block 102 where the user shapes the in-vivo model directly in the patient's mouth. It is to be understood that in an alternative embodiment, the procedure 100 may start with a previously created in-vivo model. In a further alternative embodiment, the procedure 100 may start directly with a 3D model, in which case the procedure 100 would start at block 108.

At block 104, the in-vivo model is digitized using the 3D digitizer 20. Following which, at block 106, a 3D model of the in-vivo model is created from the digitization data from block 104.

At block 108, the dental restoration material block 52 size is selected in accordance with the 3D model dimensions and, at block 110, a milling trajectory is generated in accordance with the 3D model and provided to the controller(s) 36.

Then, at block 112, the laser(s) 32 are activated and the milling of the block 52 is initiated using the optics 33 and the multi-axis displacement mechanism 40 under the control of the controller(s) 36 in accordance with the milling trajectory generated at block 110.

At block 114, the sensors 37 are used to continuously monitor the milling parameters and displacements of the intermediate model (i.e. milled block 52) during laser milling, after which, at block 116, the intermediate model data obtained from the sensors 37 are compared to the 3D model. Comparison between the intermediate model and the 3D model allows continuous adjustment and refinement of the freeform laser milling.

Then, at block 118, if the intermediate model corresponds to the 3D model, the procedure 100 ends, if not, it proceeds to block 120 where the milling trajectory is adjusted and the procedure then proceeds back to block 112.

It is to be understood that in an alternative embodiment, the procedure 100 may be used to recreate 3D models other than those of dental restoration, for example jewelry, biomaterial, semiconductor parts, etc. It is also to be understood that that laser(s) 32 will be selected according to the desire application.

Although the present invention has been described by way of particular non-limiting illustrative embodiments and examples thereof, it should be noted that it will be apparent to persons skilled in the art that modifications may be applied to the present particular embodiment without departing from the scope of the present disclosure.

The invention claimed is:

1. A system for making a dental restoration based on a 3D digital representation of a dental restoration model, comprising
    a computer for receiving the 3D digital representation of the dental restoration model and capable of creating a dental restoration milling trajectory for a selected block of given dimension and given dental restoration material, based on the 3D digital representation of the dental restoration model; and
    a laser milling apparatus in communication with the computer and capable of laser milling the dental restoration from the selected block positioned therein using the milling trajectory created by the computer, the laser milling apparatus including a multi-axis displacement mechanism for supporting and displacing the selected block, and one or more sensors for continuously monitoring a position and a dimensional evolution of the selected block and provide feedback to the computer;
wherein the milling trajectory is continuously adjusted by the computer using the feedback from the one or more sensors.

2. A system in accordance with claim 1, wherein the multi-axis displacement mechanism is located in a milling chamber of the milling apparatus.

3. A system in accordance with claim 2, wherein the laser milling apparatus includes optics associated with one or more lasers.

4. A system in accordance with claim 3, wherein the optics are provided with a pressure differential air nozzle.

5. A system in accordance with claim 3, wherein the milling chamber includes a multi-axis displacement mechanism for supporting and displacing the optics.

6. A system in accordance with claim 3, wherein the multi-axis displacement mechanism includes a plurality of parallel actuators and associated controllers for controlling the actuators in accordance with the milling trajectory.

7. A system in accordance with claim 3, wherein the multi-axis displacement mechanism includes three linear and two rotational actuators, and associated controllers for controlling the actuators in accordance with the milling trajectory.

8. A system in accordance with claim 1, wherein the computer and the laser milling apparatus are combined as a stand-alone unit.

9. A laser milling apparatus for laser milling a block of material in accordance with a milling trajectory, comprising:
    one or more lasers;
    optics associated with the one or more lasers;
    a milling chamber having therein a multi-axis displacement mechanism for supporting and displacing a block of material;
    one or more controllers for controlling the optics and the multi-axis displacement mechanism in accordance with the milling trajectory;
    one or more sensors to continuously monitor a position and a dimensional evolution of the block of material and provide feedback to the laser milling apparatus;
wherein the milling trajectory is continuously adjusted by the laser milling apparatus using the feedback from the one or more sensors.

10. An apparatus in accordance with claim 9, wherein the optics are provided with a pressure differential air nozzle.

11. An apparatus in accordance with claim 9, wherein the multi-axis displacement mechanism includes a plurality of parallel actuators.

12. An apparatus in accordance with claim 9, wherein the multi-axis displacement mechanism includes three linear and two rotational actuators.

13. A method for making a dental restoration, comprising:
    producing a 3D digital representation of a dental restoration model;
    selecting a block of dental restoration material having a size sufficient to encompass the dental restoration;
    creating a dental restoration milling trajectory of the dental restoration for the selected block based on the 3D digital representation of the dental restoration model;
    positioning the selected block in a laser milling apparatus;
    laser milling the dental restoration from the selected block in accordance with the milling trajectory; and
    continuously monitoring a position and a dimensional value of the selected block and adjusting the milling trajectory based on feedback provided by the monitoring of the laser milling of the selected block.

14. A method in accordance with claim 13, wherein the laser milling apparatus is in accordance with the laser milling apparatus of claim 9.

* * * * *